(12) United States Patent
Hansen et al.

(10) Patent No.: US 8,231,580 B2
(45) Date of Patent: Jul. 31, 2012

(54) ACCESS PORT

(75) Inventors: Michael Hansen, Gilleleje (DK); Peter Muellejeans, Aalsgaarde (DK); Bent Hall Jensen, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 481 days.

(21) Appl. No.: 11/988,380

(22) PCT Filed: Jul. 7, 2006

(86) PCT No.: PCT/DK2006/000401
§ 371 (c)(1),
(2), (4) Date: Mar. 11, 2009

(87) PCT Pub. No.: WO2007/006306
PCT Pub. Date: Jan. 18, 2007

(65) Prior Publication Data
US 2009/0192467 A1    Jul. 30, 2009

(30) Foreign Application Priority Data

Jul. 8, 2005  (DK) .................................. 2005 01008
Dec. 23, 2005  (DK) .................................. 2005 01829

(51) Int. Cl.
*A61M 5/32* (2006.01)
(52) U.S. Cl. .................. 604/174; 604/180; 604/179
(58) Field of Classification Search ................. 604/174, 604/179, 180, 171
See application file for complete search history.

(56) References Cited

U.S. PATENT DOCUMENTS

| | | | |
|---|---|---|---|
| 3,487,837 A | 1/1970 | Petersen | |
| 3,856,020 A | 12/1974 | Kovac | |
| 3,882,853 A | 5/1975 | Gofman et al. | |
| 4,589,185 A | 5/1986 | Schneider | |
| 4,755,173 A | 7/1988 | Konopka et al. | |
| 4,767,411 A | 8/1988 | Edmunds | |
| 4,897,081 A * | 1/1990 | Poirier et al. | 604/175 |
| 5,073,169 A | 12/1991 | Raiken | |
| 5,176,648 A | 1/1993 | Holmes et al. | |
| 5,215,531 A * | 6/1993 | Maxson et al. | 604/180 |
| 5,354,283 A * | 10/1994 | Bark et al. | 604/180 |

(Continued)

FOREIGN PATENT DOCUMENTS

| | | |
|---|---|---|
| EP | 0 039 183 A1 | 11/1981 |
| EP | 1344539 | 3/2003 |
| EP | 1 433 494 A1 | 6/2004 |
| JP | 56-42560 | 4/1981 |
| JP | 61-125846 | 8/1986 |
| JP | 2001-324018 | 11/2001 |

(Continued)

OTHER PUBLICATIONS

English translation of JP Office Action dated Jun. 15, 2010.

*Primary Examiner* — Kevin C Sirmons
*Assistant Examiner* — Brandy C Scott
(74) *Attorney, Agent, or Firm* — Coloplast Corp., Coloplast A/S; Daniel G. Chapik; Nicholas R. Baumann

(57) ABSTRACT

An access port for enabling passage of a conduit through a partition wall, said port comprising three portions, a sleeve portion surrounding an aperture for receiving a conduit there through, a flange portion for attachment to the partition wall, said flange portion encircles the sleeve portion and has a greater diameter than the sleeve portion, and a membrane portion connecting the flange portion and the sleeve portion. The port may be suitable for, in a leak-proof manner, passing a catheter or drain tube through the wall of a medical device such as a wound care device or a drainage bag.

38 Claims, 13 Drawing Sheets

U.S. PATENT DOCUMENTS

| | | | |
|---|---|---|---|
| 5,366,446 A | 11/1994 | Tal et al. | |
| 5,626,597 A | 5/1997 | Urban et al. | |
| 5,752,938 A * | 5/1998 | Flatland et al. | 604/167.01 |
| 5,807,341 A | 9/1998 | Heim | |
| 5,848,992 A | 12/1998 | Hart et al. | |

FOREIGN PATENT DOCUMENTS

| | | |
|---|---|---|
| JP | 2003-334243 | 11/2003 |
| WO | WO 92/19298 | 11/1992 |
| WO | WO 93/25264 | 12/1993 |

* cited by examiner

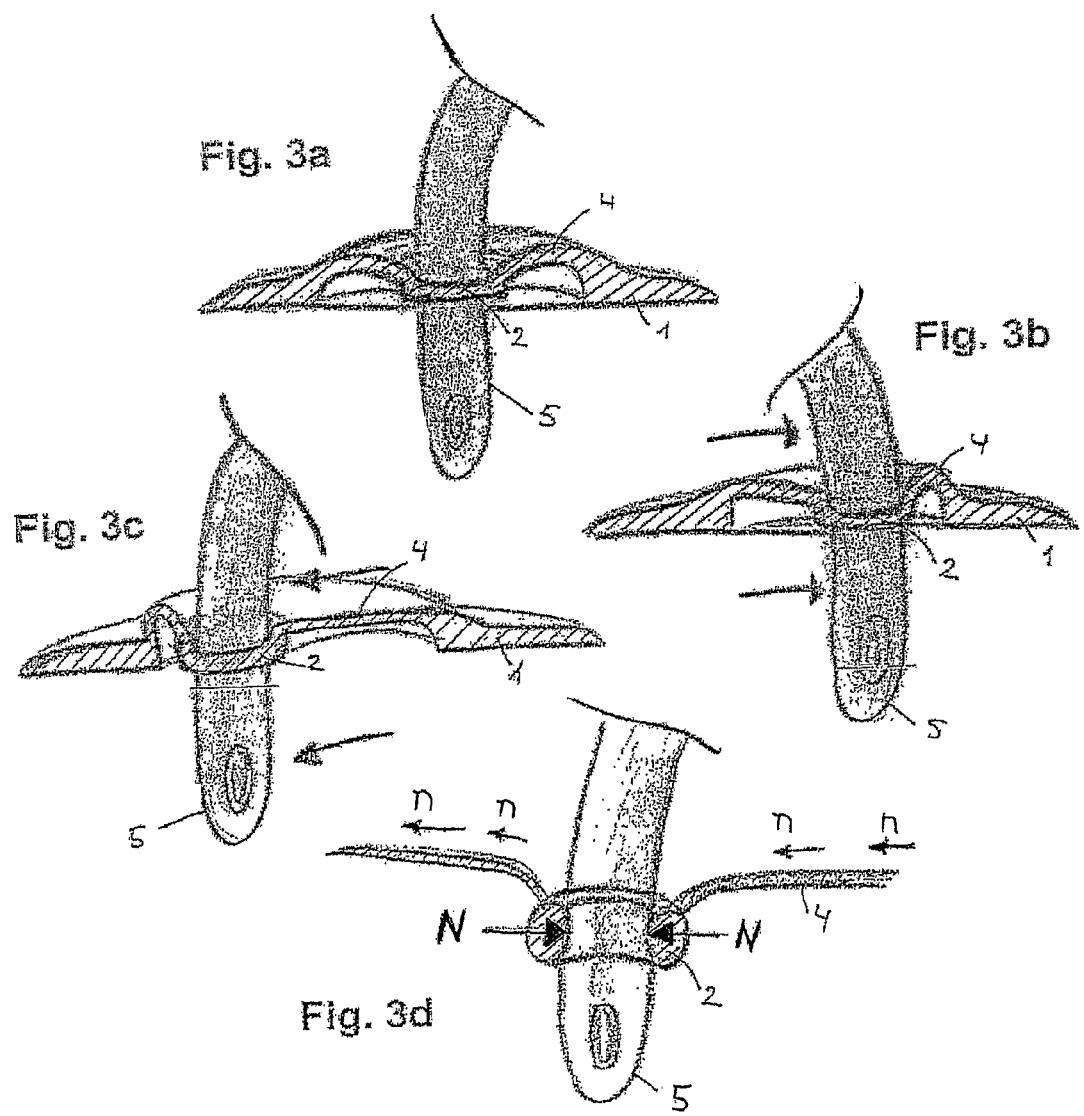

ACCESS PORT

This is a national stage of International application No. PCT/DK2006/000401 filed on Jul. 7, 2006 and published in English.

BACKGROUND OF THE INVENTION

1. Field of the Invention

The invention relates to an access port for providing a leak proof seal between a conduit and a partition wall such as a film layer of a medical device or the skin.

2. Description of the Related Art

It is often desired to lead a conduit, such as a drain tube, catheter, trocar or the like through a barrier, such as a flexible film, the wall of an ostomy bag or the skin surface, e.g. laparoscopy in a leak proof manner. Access ports for such purposes are well known in the art. Several problems may be associated with these access ports: Flexibility allowing the conduit to enter different positions under control, adapting the size or the aperture for the conduit to fit different conduit diameters, attachment to the surface and avoiding leakage.

In U.S. Pat. No. 5,215,531 is disclosed a cannula skirt for stabilizing and restraining the movement of a laparoscopic cannula as well as providing a leakage tight seal against the patients skin. The skirt comprises a narrow stem segment for securing the cannula and a wider flanged section for attachment to the skin by adhesive means. The skirt provides flexibility for the cannula to move slightly sidewards, while up and down movements is controlled. The skirt is provided with a clamp for securing tight fit around the cannula.

In U.S. Pat. No. 4,589,185 is disclosed a drain access port mounted on a thermoplastic film, such as the wall of an ostomy bag. The access port comprises an elastomeric nipple portion and a rigid portion for attaching the port to the thermoplastic film. The nipple portion is preferably cone-shaped and the nipple portion of the access port needs to be cut to fit the catheter. The drain access port can only be accessed from one direction. If the user tries to access the port with a catheter form the other side, there is a risk of separating the two parts during use. In the operation the operator has a risk of cutting the opening to big, this will give a poor seal around the catheter. Furthermore after having adjusted the nipple portion to a certain catheter size, good seal around a smaller catheter cannot be achieved. The limited elasticity or stretchability of the material jeopardizes the introduction of anything into the drains access port that is considerably bigger than the aperture that the user have cut from start. The device includes internal and external coupling rings adapted to be locked together with a collar of film material clamped there between. The rigidity of this clamping portion increases the risk of kinking the conduit (e.g. a catheter), because it is made of two rigid injection molded parts and thus not flexible.

Alcare has a product on the market, much similar to the above-mentioned product, but without a rigid base part, as the product is attached to the film with adhesive. However, the material is not flexible enough to introduce something into the drain access port that is just a little bigger than the opening the user has cut from start as the flexibility of the material is to low. This makes it difficult to insert something slightly bigger than the opening created by the cut. Due to that it feels more difficult to insert a catheter that is just slightly bigger than the opening, the user have tendency to cut the opening even bigger, increasing the risk of poor sealing.

The above-mentioned devices need a (sterile) scissor or other cutting instrument for making a hole and it may be a problem to have such sterile scissors available. Cuffing with non-sterile scissors may lead to infection of the site.

The above-mentioned references all suffer from problems with leakage and/or flexibility and thus there is still a need for a leakage-proof and flexible access port.

SUMMARY OF THE INVENTION

One object of the present invention is to provide a drain access port being capable of securing a leak proof seal between a conduit and a partition wall.

Another object of the invention is to provide a port that is accessible for multiple sizes of drains or tubes.

Yet another object of the present invention is to provide an access port that is discrete, flexible and easy to use.

Still another object of the invention is to provide an access port that can be welded to a partition wall.

Yet another object is to provide a closure of an access port that may easily be opened without use of tools.

Still another object is to provide is to provide an access port that reduces the risk of kinking the conduit.

The access port of the present invention may achieve these and other objects.

BRIEF DESCRIPTION OF THE DRAWINGS

The invention is disclosed more in detail with reference to the drawings in which FIG. 3 shows an embodiment with a catheter inserted.

DETAILED DESCRIPTION OF THE PRESENT INVENTION

Figure 1:
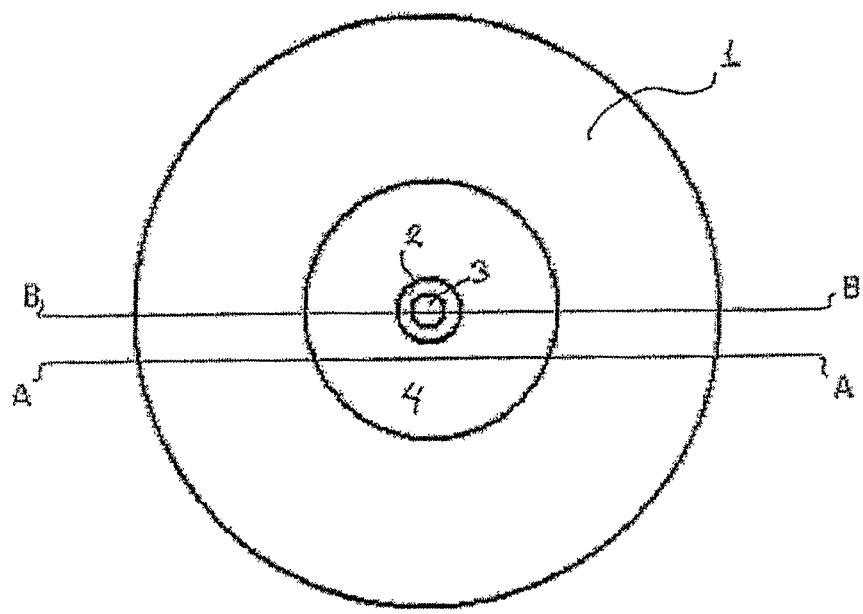
FIG. 1 shows an embodiment of the invention seen from below.

The invention relates to an access port for enabling passage of a conduit through a partition wall, said port comprising three portions, a sleeve portion surrounding an aperture for receiving a conduit there through, a flange portion for attachment to the partition wall, said flange portion encircles the sleeve portion and has a greater diameter than the sleeve portion, and a membrane portion connecting the flange portion and the sleeve portion, the sleeve portion comprises an upper sleeve lip extending upwards and a lower sleeve lip extending downwards with respect to the point where the membrane portion and the sleeve portion connects.

In a preferred embodiment of the invention the lower sleeve lip may be longer than the upper sleeve lip. Upward with respect to the present invention is the direction pointing away from the surface contacting the partition wall, where downward is pointing towards the partition wall.

In another embodiment of the invention the upper sleeve lip is longer than the lower sleeve lip. In a third embodiment of the invention the sleeve lips are approximately the same length.

Preferably, the sleeve portion is of substantially uniform thickness.

It is preferred that at least one of the sleeve lips is capable of turning inside out during use. When a conduit is entered through the sleeve portion, the sleeve lip of the side from where the conduit is entered may be dragged, due to friction forces, with the conduit, thus inverting the sleeve lip to turn inside out and create a double layer of the upper end the lower sleeve lips. When the conduit is positioned the conduit may be dragged a little backwards, thus inverting both sleeve lips to point the opposite way. The double layer of sleeve lips controls the conduit and facilitates a perfect sealing around the conduit.

The invention also relates to an access port for enabling passage of a conduit through a partition wall, said port comprising three portions, a sleeve portion surrounding an aperture for receiving a conduit there through, a flange portion for attachment to the partition wall, said flange portion encircles the sleeve portion and has a greater diameter than the sleeve portion, and a membrane portion connecting the flange portion and the sleeve portion, wherein the membrane portion has a width of at least 60% of the diameter of the aperture of the sleeve.

The width of the membrane portion is measured as the distance from the point where it is connected to the sleeve portion to the point where it is connected to the flange portion. If the membrane portion is circular and the width of the membrane portion equals the diameter of the sleeve portion, then the diameter of the membrane portion will be approximately three times the diameter of the sleeve portion.

The width of the membrane portion may be at least 75% of the diameter of the aperture of the sleeve, more preferred at least 90%, even more preferred at least 100% of the diameter of the aperture of the sleeve.

In one embodiment of the invention the width of the membrane portion is at least 110% of the diameter of the aperture of the sleeve.

The membrane portion facilitates flexibility of the port by providing an elastic connection between the sleeve portion and the flange portion. When a conduit is inserted through the sleeve portion and the conduit is moved, the elasticity of the membrane portion facilitates easy movement without disturbing the tight fit of the sleeve portion to the conduit. The forces of the membrane portion, pulling the sleeve portion, are weaker than the forces of the sleeve portion, pulling the conduit. Leakage-proof sealing and high flexibility is thus achieved.

In the treatment of wounds or fistulae or situations where a conduit has to enter a natural or artificial opening of the body in a fluid-tight manner, the user has a need for accessing the wound or opening with a catheter through an access port, having a perfect seal around the catheter. The catheter/drainage tube for entering through the access port may have different dimensions, dependent on the use. E.g. catheters for wound drainage may have a size in the range of minimum Ø4 mm (CH12)-normal catheter size used Ø8 mm (CH24)-maximum catheter used Ø17 mm (CH51). Thus an access port has to be capable of handling different conduit sizes and still provide a leak-proof seal.

The access ports known in the art are provided with a standard aperture or the aperture may be enlarged by use of cutting means such as a pair of scissors. However the adaptation of the aperture may be laborious and when the catheter is exchanged with a catheter of a smaller diameter, the aperture will be too big and leakage may occur.

The present invention may overcome the above-mentioned weaknesses; in terms of eliminating risk of cutting a too big hole in the access port, leading to poor sealing around the catheter, plus having a very flexible access port with no risk of kinking the catheter during use, and at the same time giving the user a high capability of fitting within the same access port making perfect seal around a broad spectrum of catheter sizes, tubes etc. used during treatment of wounds, fistula etc. Provided the proper choice of material, the port may be able to seal effectively against conduit sizes varying over a range of 10 to 1. The aperture of the access port may be opened without use of tools, and is thus time saving for the user.

In one embodiment of the invention the access port may be mounted on the ostomy or wound care product at delivery, ready for use when the aperture is opened. Such port may be applied by welding or by use of adhesive. The port may be placed at standard positions for the intended purpose and is thus ready for use at once. Such solution is less time-consuming, the user only have to open the aperture to make an access opening in the access port. This makes the access port of the invention more hygienic, with no need for a cut from sterile scissors thus minimizing the risk of contamination during cutting of the aperture.

The access port of the invention is designed to provide perfect seal to various sizes of conduits. The aperture of the port is capable of adapting to various conduit sizes and still provides good sealing, and thus there is no risk of cutting the aperture to big. Due to the construction and thermoplastic characteristics of the port it is possible to established good seal around a small catheter after having used a bigger catheter.

In the treatment of wounds, especially chronic wounds, vacuum-therapy may be used. The wound is covered with a gastight cover layer, such as a polymer film, and a drain tube is inserted into the wound and vacuum is applied through the tube. The exposure to reduced pressure or vacuum promotes wound healing and exudates may be drawn away through the tube. The critical point in this treatment is that the access of the tube through the cover layer is a gas-tight manner. The access port of the present invention is very suitable for this purpose as it both provides a leak proof seal as well as kinking of the tube will be avoided.

The partition wall may be any barrier, such as a flexible film of medical device such as an ostomy or drainage bag, a wound dressing or the partition wall may be the body surface. The port of the invention may also be used for providing a leakage proof access through natural or artificial body openings, e.g. in connection with intermittent and/or indwelling catheter, for rectal access/bowel management, urethral access or suprapubic access.

The conduit may be any desired conduit for leading a fluid and or instrument (e.g. laparoscopy) from one side of the wall to the other. Examples of such conduits may be catheters, drainage tubes, trocars etc.

The presence of the sleeve portion is important for obtaining a good sealing around the conduit. The perfect seal is obtained as long as the forces from the sleeve portion towards the center of the port overcome the forces away from the center of the membrane portion.

The sleeve portion has preferably a thickness at least equal to the thickness of the membrane portion. In one embodiment of the invention the sleeve portion is thicker than the membrane portion.

The membrane portion has preferably a substantially uniform thickness. However, the thickness of the membrane may vary over the area, as long as the desired flexibility is achieved. It may be preferred that at least 50%, more preferred 75% and most preferred 90% of the membrane portion has a thickness equal or thinner than the thickness of the sleeve portion.

It is preferred that the inner diameter of the flange portion substantially corresponds to, or is wider, the diameter of the membrane portion. This leaves room for flexibility, e.g. when a conduit is mounted in a substantially horizontal position. The flange portion is flexible and capable of adapting to position of the conduit, e.g. when the conduit is placed in a horizontal position thus removing the risk of kinking the conduit.

The conduit may pierce the access port from both sides. Typically, a catheter is entered, with the tip portion in front, from the outside and into the wound site or bag. The tip portion of such catheter is usually rounded and smooth for facilitating penetration into the body and may be easy to pass through the port.

However, in many cases, the tip of the catheter or drainage tube is already inserted in the wound or body part and thus it will be the other end of the catheter or tube that has to pass the port. This end of the conduit may however often be provided with a voluminous and often quite rigid connector part for connecting one or more conduits to the catheter or tube. This connector part is difficult or even impossible to pass through access ports known in the art, and if succeeded, the aperture of the port will be so enlarged and damaged that a tight seal against the conduit is no longer possible. The access port of the present invention is capable of passing items of the size of such connectors and still return to it original size afterwards and provide a safe and leak proof seal.

The flexible design has a built-in ability to distribute the forces within the material of the membrane connecting the flange and the sleeve portion. This may be obtained by assuring at least some flexibility of this surrounding membrane portion, e.g. by having some extra material, such as through injection molding of the membrane in a non-linear configuration such as a slight curve. This flexibility, inherent in the construction of the port, may allow some movement of the sleeve portion before the surrounding membrane actually begins to be stretched, and hereby begins to build up forces, that works against the perfect seal made by the sleeve portion in the center of the port.

The access port of the present invention may be prepared from any suitable material having the appropriate properties with respect to flexibility, elasticity and strength. Examples of such materials are silicone materials, thermoplastic elastomers, vulcanized rubber materials or blends/copolymer materials. Foam materials like silicone foams, PU-foams, PE-foams or vulcanized rubber foam may also be used. The material should be very flexible, highly elastic, exhibit a high elongation, i.e. relative soft materials defined by the Shore A scale would in many cases be suitable.

It is preferred that the elongation is between 200 to 1000% and the hardness is between 30 to 40 Shore A. The densities may vary depending on the base polymer. For PE modified materials typical values may be between 0.86 and 0.90 g/cc, for SEBS based materials up to 1.1 g/cc.

In this context elongation means the short-term elongation of the material from which it will substantially regain the original shape when the stress inducing the elongation is removed.

The material may have a hardness of between 30 and 40 Shore A, more preferred between 30 and 35 Shore A.

The density of the material may be between 0.8 g/cm$^3$ and 1.2 g/cm$^3$, more preferred between 0.85 g/cm$^3$ and 1.1 g/cm$^3$ and most preferred between 0.85 and 1.0 g/cm$^3$.

The material may preferably have an elongation of at least 200%, more preferred at least 400% and most preferred at least 600%. In one embodiment of the invention the material has an elongation of at least 700%.

In a preferred embodiment of the invention the material of the access port has an elongation of 800%, a hardness off 33 Shore A and a density of 0.9 g/cc.

In a preferred embodiment of the invention the material comprises SEBS (styrene ethylene butylene styrene block copolymer). The material may be a SEBS as the one sold by Wittenburg BV under the registered trade name Cawiton Med PR 3132.

The access port is designed with soft, flexible edges of the flange portion that can bend, fold up, twist or in other words change shape and configuration, minimizing the risk of kinking of the catheter.

It may be preferred that the access port of the present invention has a generally flat design, thus achieving a discrete appearance without substantial protruding parts. Thus the port may be fixed onto the product from supplier and due to the discrete design it will not interfere with the functionality of the product if the port is not in use. By having a fixed positioning the user neither needs to make an aperture in the product, nor consider positioning this onto the product. Preferably, the height of the access port of the present invention is smaller than the width of the port.

The port may preferably have a slightly curved design of the membrane portion assuring extra flexibility to the membrane that surrounds the center sleeve portion as well as a smooth appearance.

The flange portion has preferably a substantially flat surface contacting the partition wall in order to provide a snug fit. However, the surface of the flange may be curved or otherwise adapted to fit to curved or irregular surfaces.

It has surprisingly been shown that the access port of the present invention is highly capable of fixing the conduit, i.e. holding the conduit in position so it does not move unintentionally inwards or outwards when inserted in the port. Due to the design of the access port, the sleeve seems to "lock" the conduit, thus impeding sliding through the port, especially when the conduit is having an angle to the plane of the flange of less than 90 degrees.

The "locking" effect of the device is controlled partly by the design of the port and partly by the choice of material of the port. The flexibility and elasticity of the material has an impact on this locking effect, which optionally may be further increased by a high friction surface of the port and the helping forces coming from the design of the sleeve portion.

When the conduit is moved up and down in the port a certain resistance is also met, the resistance coming from the forces squeezing the sleeve around the catheter. But the resistance is significantly lower when the conduit is held in a vertical position with respect to the port, compared to when the conduit is resting in a substantially horizontal position. The locking function is more predominant in the horizontal position thereby securing the position of the catheter in the position of normal use.

As mentioned above, the design of the sleeve portion plays an important role for the locking effect, and also the sealing effect of the sleeve against the catheter or tube depends may also be influenced by the design of the membrane portion surrounding the sleeve. It has proven expedient to make the sleeve as a cylinder having a wall thickness at least equal to the thickness of the central part of the membrane portion and having a length longer than the same thickness. This will provide for a sealing force distribution as mentioned above. In a preferred embodiment the relation between length of the sleeve portion and the wall thickness of the sleeve portion may be at least 2:1, more preferred at least 5:1 and most preferred at least 10:1.

The longer the sleeve portion is, the lower risk of leakage. However, a long sleeve portion may render it difficult to insert the conduit. Catheters for wound drainage may have a size in the range of Ø4 mm (CH12) to Ø17 mm (CH51). For such catheters it may be preferred that the total length of the sleeve portion is at least 6 mm, more preferred at least 8 mm and most preferred at least 10 mm.

To achieve good sealing effect against the conduit, the dimensions of the sleeve portion are important. The length of the sleeve portion, the thickness of the wall of the sleeve portion and the diameter of the aperture may be balanced to obtain the leakage proof seal. Preferably, the relations between the diameter of the aperture and the length of the sleeve portion is at least 1:1, more preferred 1:1.25, even more preferred 1:1.5 more preferred 1:1.75 and most preferred 1:2. It may be preferred that the length of the sleeve portion is larger than the diameter of the aperture.

The thickness of the wall of the sleeve portion may preferably be less than the 50%, more preferred less than 30%, even more preferred less than 20% and most preferred less than 10% of the length of the sleeve portion. Preferably, the relation between the thickness of the wall and the diameter of the aperture is at least 1:4, more preferred at least 1:6, even more preferred at least 1:8 and most preferred at least 1:10.

However, designing the port with a central aperture having a diameter significantly smaller than the diameter of the conduit a smaller thickness or even leaving out the sleeve entirely will also yield an effective seal, but at the price of a less effective lock. In this construction, adding ribs to the membrane portion at a position corresponding to the diameter of the conduit will again improve the locking effect.

For closing the opening of the sleeve adapted to take up the catheter the access port may comprise a closing device, e.g. an adhesive label or a plug.

In one embodiment of the invention the access port of the present invention may comprise a plug, said plug being capable of closing the aperture of the sleeve. The plug may be a separate unit, which may be inserted in the aperture in a leak proof manner, but preferably the plug is an integrated part of the port. The sleeve portion may be elongated vertically into a plug portion. Before insertion of a conduit the plug is removed. The plug may be removed by the use of cutting tools, such as scissors or a knife, but preferably the plug is adapted to be removed by grabbing the plug with the fingers and pulled until the material breaks and the plug is separated from the port. In order to control the separation the elongated part of the sleeve connecting the sleeve and the plug may be provided with a breaking line, e.g. in the form of a weakening line such as a ridge or groove where the material is intended to break. The weakening line may advantageously be visible.

The breaking line or weakening line may be right next to the plug or it may be in a distance from the plug, facilitating the separation. When the plug is removed, the port is ready for use. The plug may be discarded or it may be reused as a plug for sealing the port if the conduit is removed.

It may be preferred that the plug and the access port are made of the same soft material or only varying slightly in softness. By making the two parts having equal material characteristics, a closure mechanism having superior resistance against outside influences is achieved. The plug may then move together with the drain access ports movement, assuring the best possible seal.

The access port of the present invention may be provided with an adhesive layer for attachment to the partition wall. A release liner that is removed before application may protect such adhesive layer. By providing the port with adhesive means it may be easy for the user to apply the port at the exact desired location.

In another embodiment of the invention the port may be welded to the partition wall. This may be advantageous as a welding often is stronger than adhesives, and thus the port is not easily detached during use. The port may be welded to the partition wall during production of the article having the wall, and the wall may be provided with several ports, rendering it possible for the user to choose the port having the best location for the purpose. The unused ports may, due to their discrete design stay on the wall without causing any inconvenience.

When applying the port of the invention to a film layer, such as a wound dressing or a bag, the port may be applied by welding or by use of adhesive. The film may be provided with an aperture or an aperture may be cut before or after the application.

Most materials will change properties over time and temperature. A starting aperture designed for easy access of a specific range of catheters, may begin to loose its grip due to this change of properties, resulting in a decrease in the force [N] transferred from the sleeve to the catheter making the seal.

To compensate for this, the sleeve may be provided with a portion extending downwards to assure optimum seal at high pressures (0.01 bar or lower-up to at least 0.15 bar). By assuring the sleeve cannot be pulled up during use, the access port significant increases in how much the drain port can seal even after having been stored at high temperature.

In a preferred embodiment of the invention the sleeve portion comprises sleeve lips extending both upward and downward. The sleeve portion will thus extend both upwards and downwards from the point where the sleeve portion is connected to the membrane. This design has showed some improvements compared with same design where the sleeve portion only extends in one direction. The risk of leakage during normal use may be lowered by this optimization of the design.

The improvement has been achieved by having a sleeve portion comprising sleeve lips extending in both directions is believed to arise from the extra force [N] coming from the double wall thickness, that is created in the center, when the lip from one side is inverted and making both the upper and the lower lip to be positioned in the same direction and at least partly on top of each others.

A very short sleeve portion may increase the risk of leakage, while a too long sleeve portion may jeopardize easy insertion of the conduit. To assure an easy insertion, it is preferred that the starting aperture is not significantly smaller than the diameter of the catheter. Having an access port with a starting aperture of e.g. 5 mm, a sleeve length of 12 mm, may render insertion of a large catheter, such as a CH32, Ø10 mm catheter difficult, especially if the friction between the catheter and the access port material is high. Wetting the catheter surface may improve the passage.

In one embodiment of the invention the access port is provided with a sleeve portion wherein the upper sleeve lip has diameter different from the lower lip. The upper or lower lips may be provided with a weakened line, facilitating easy removal of a part of the sleeve portion. The same port may thus easily be adapted to receive both small catheters and big catheters and the adjustment of the port may be facilitated without using a pair of scissors or other cutting tools.

The observation of having a longer sleeve portion and hereby moving towards a more leak proof design, in combination with the idea of removing a piece of the access port by pulling, making it possible to adjust the opening making the insertion of a wider range of catheters possible and more easy without using a pair of scissors (using a par of scissors will only increase the risk of pinholes, uneven cuts and wrong cut in terms of the length of the sleeve increasing the risk of leakage etc.).

Due to the incorporated break function and the flexible design, the safety is high, especially if the user ensures that catheter is inserted into the access port as illustrated FIG. 7, with the sleeve position downwards and then fixated to the product. Should the fixation loose its grip, the sleeve will give some resistance, working against this unintended pull. The break function will in this case increase the security and prevent the catheter form sliding out of the port, and further more preventing the sleeve from going from a downwards position to a upwards position, hereby minimizing the risk of leakage.

DESCRIPTION OF THE PREFERRED EMBODIMENTS

The invention is now explained more in detail with reference to the drawings showing preferred embodiments of the invention.

FIG. 1 shows an embodiment of the invention, seen from below. The port comprises a flange portion (1) for attaching to the surface to be penetrated, a sleeve portion (2) with a central aperture (3) for receiving the conduit and a membrane (4) connecting the sleeve portion (2) with the flange portion (1).

Figure 2:
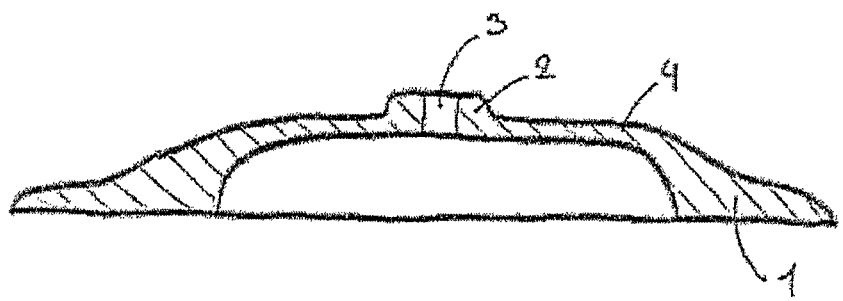
FIG. 2 shows the same embodiment in cross-section.

FIG. 2 shows the same embodiment of the invention in cross-section. The flange portion (1) encircles the sleeve portion (2) with the aperture (3). The two portions are connected with the membrane (4). The thickness of the sleeve portion (2) is preferably larger than the thickness of the membrane portion (4) in order to provide a tight seal against the conduit. Furthermore, the flange portion (1) may be thicker than the membrane portion (4) facilitating more rigidity.

FIGS. 3b-e show a cross-section along the A-A line of FIG. 1 of a port of the invention, with a catheter (5) inserted. FIG. 3b shows the catheter (5) centered in the port, and the membrane portion (4) is substantially relaxed. FIG. 3c and 3d disclose the catheter (5) forced sideward in the port, thus exerting a force to the stretched part of the membrane portion (4). FIG. 3e shows in detail the forces acting on the catheter (5) and the port, wherein the force N is the force with which the sleeve (2) is compressing the catheter (5) and n is the force that the membrane portion (4) is subjected to when the catheter (5) is moved. As long as the force N is larger than the force n, the port will provide a leak proof seal against the catheter (5). The presence of the sleeve portion (2) will keep N larger than n. A port without a sleeve, in the form of a membrane provided with an aperture without a sleeve portion (2), will not be able to provide a leak proof seal against the catheter (5) as the force n will be larger than the force N, as there is no sleeve portion squeezing around the catheter. The forces N and n are controlled by the design of the port and the choice of material for the access port.

Figure 4A:
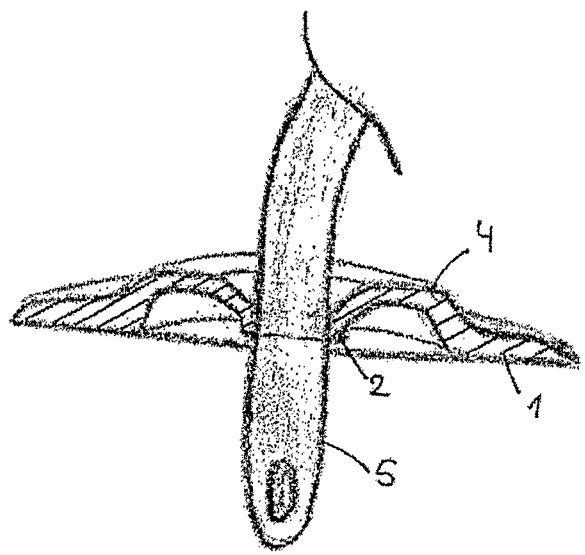
FIG. 4 shows an embodiment with a horizontal catheter, FIG. 5 show a number of embodiments of the invention.
Figure 4B:
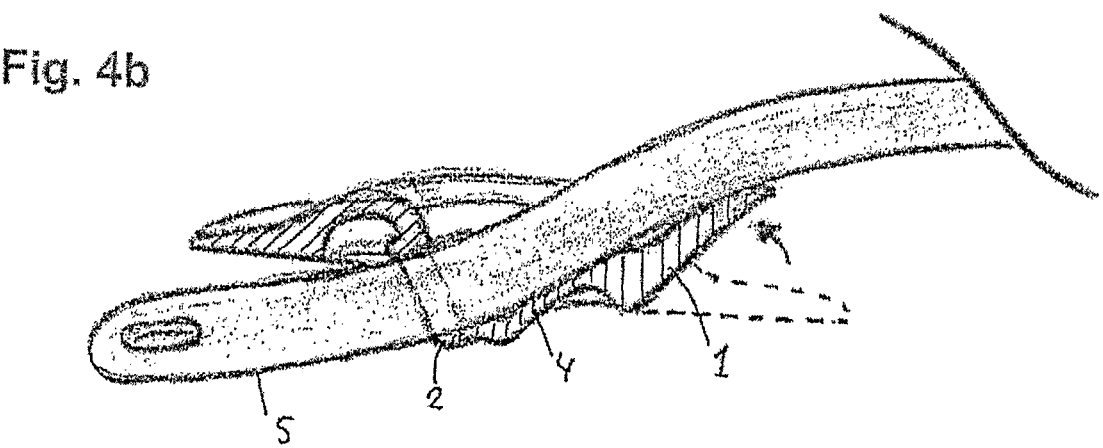

FIGS. 4a and 4b disclose the locking effect of the access port of the invention. The catheter (5) inserted in the port in a substantially vertical configuration may be moved longitudinally with respect to the catheter when subjected to moderate forces, FIG. 4a. When the catheter (5) is lowered into a substantially horizontal configuration, which often will be the case while in use, a part of the port will be exerted to pressure from the catheter (5) which will force the membrane portion (4) down and tip the flange portion (1) up, resulting in a quite large contact area between the port and the catheter (5). If the surface of the port is provided with a certain friction, the large contact surface may result in a high resistance and it will be difficult to slide the catheter (5) in longitudinal direction. Thus the catheter (5) will be locked in the position unless it is exposed to large forces. As can be seen from the FIG. 4b, no risk of kinking the catheter (5) may arise, as the flexibility of the port absorbs the movements.

Figure 5A:
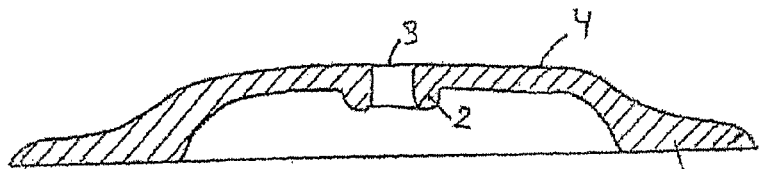
Figure 5B:
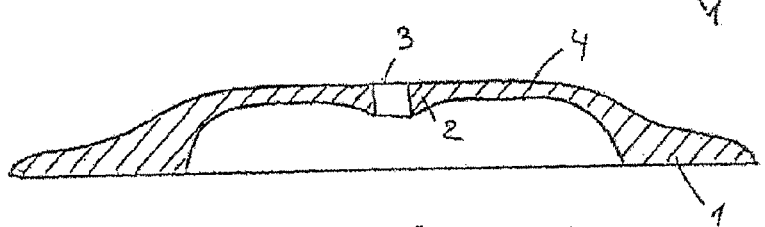
Figure 5C:
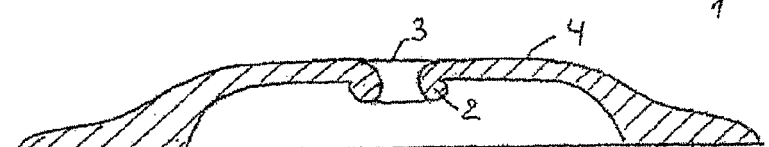
Figure 5D:
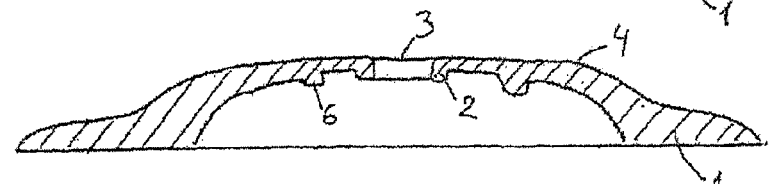
Figure 5E:
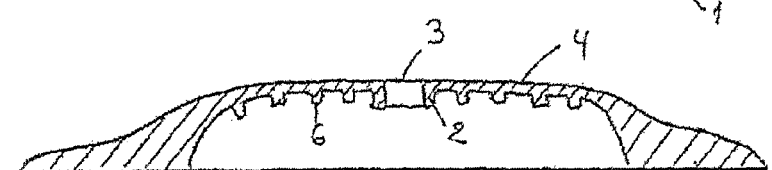
Figure 5F:
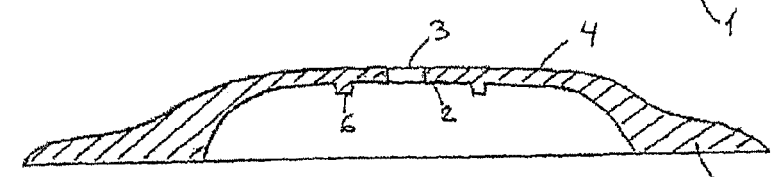
Figure 5G:
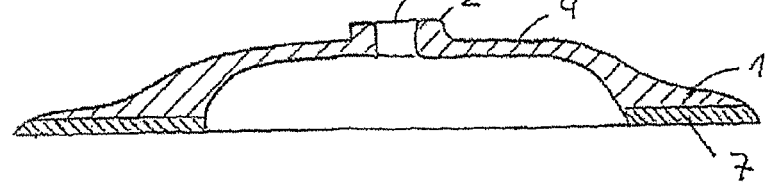
Figure 6A:
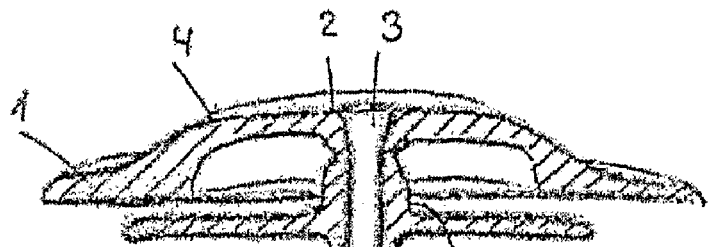
FIG. 6 shows an embodiment of the invention with a plug.
Figure 6B:
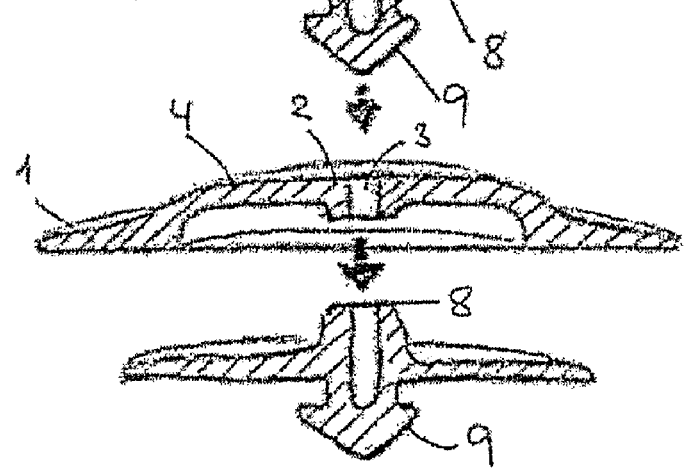
Figure 6C:
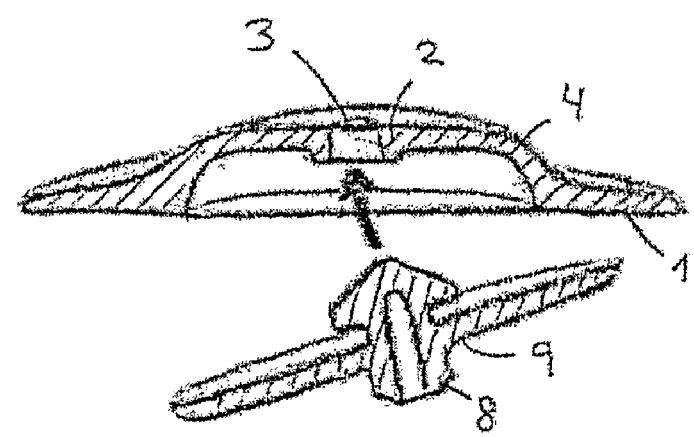
Figure 6D:
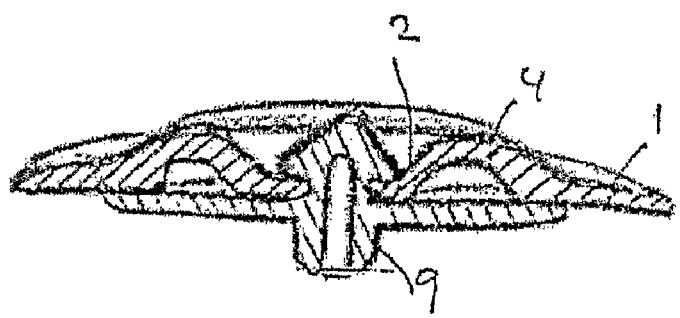

FIGS. 5a-5g disclose different embodiments of the invention with regard to the shape of the sleeve portion (2) and the membrane portion (4). In FIG. 5a is shown an embodiment where the sleeve (2) is extending downwards, in direction of the partition wall to which it may be applied. The thicker layer of material at the sleeve portion (2) secures that the force N is higher than the force n. FIG. 5b disclose a solution where the thickness of the material increases continuously from the membrane portion (4) to the sleeve portion (2). FIG. 5c disclose a sleeve portion (2) in the form of a roll. FIGS. 5d and 5e disclose the presence of ribs (6) at the membrane portion (4), either organized as concentric circles or as a helix. The ribs (6) are shown on the wall-facing surface of the membrane portion (4), but could just as well be located on the upper surface of the membrane portion (4). FIG. 5f disclose a solution for large conduits, where the sleeve portion (2) is diminished, and instead a concentric rib (6) is provided at a distance from the aperture (3). This embodiment is not suitable for small diameter conduits, but may be for larger conduits, having a diameter greater than the diameter of the rib (6), and they may be easier to enter into the port. FIG. 5g disclose an embodiment similar to the one in FIG. 5a, but where the sleeve portion (2) is extending away from the wall. In FIG. 5g the flange portion (1) has been shown as prepared from two different materials (1,7), e.g. a softer material for the sleeve portion (2) and the membrane portion (4) and a more rigid for the flange portion (1) or to achieve better welding properties or attachment of adhesive etc.

FIGS. 6a-d disclose an embodiment comprising a plug (9). The sleeve portion (2) of the port is extending into a plug (9). The plug (9) may be detached by pulling the plug (9) and the port away from each other until the material breaks at a weakened line (8). The plug (9) may be designed in such a way that it may be used for resealing of the port by inserting the plug (9) into the aperture (3). In this embodiment of the invention the plug (9) is shown extending downwards but a solution where it is extending upwards may also be possible or even preferred as the plug (9) then will be located at the outer surface of the wall and will thus be easier to reach.

Figure 9A:
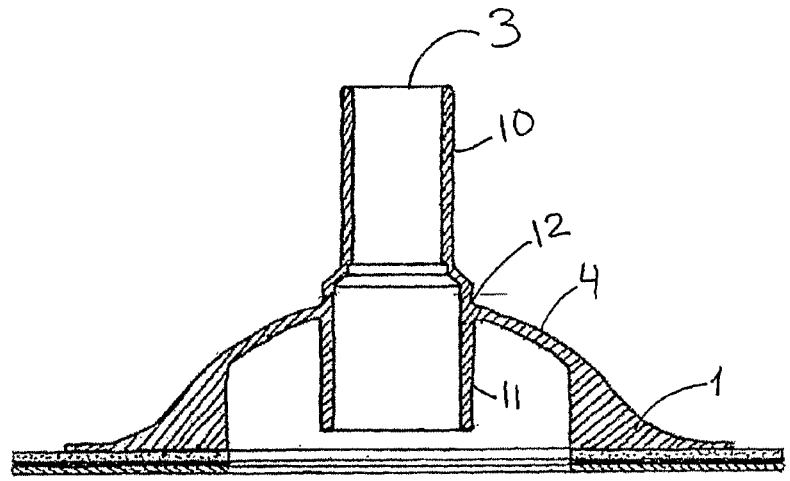
FIGS. 9a and 9b show an embodiment of the invention and FIGS. 10a-10d show embodiments of the invention.
Figure 9B:
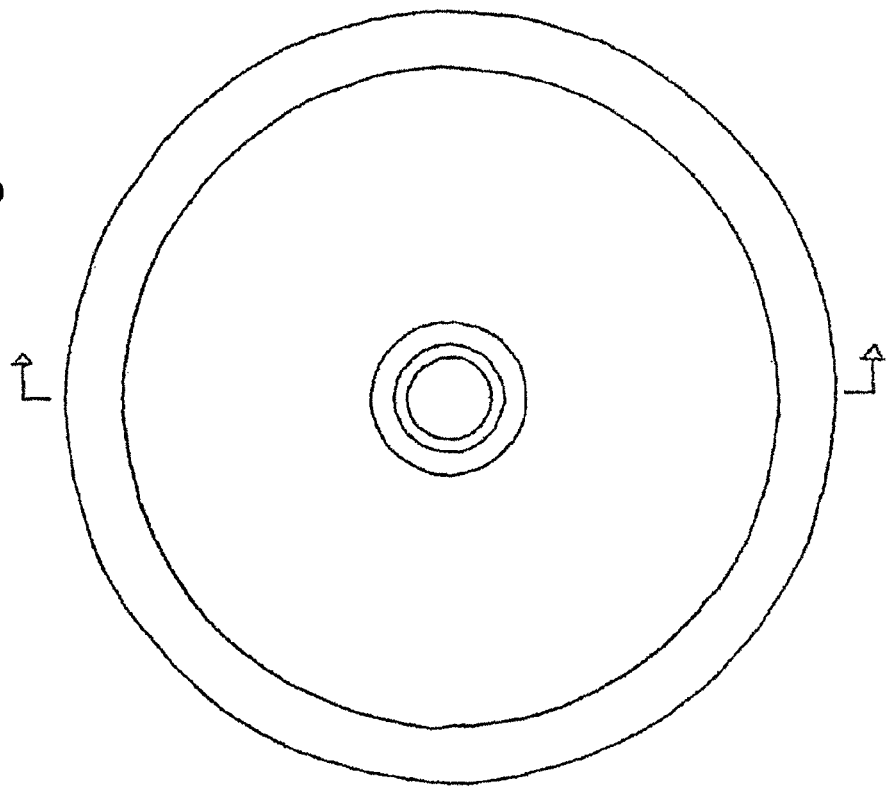
Figure 10A:
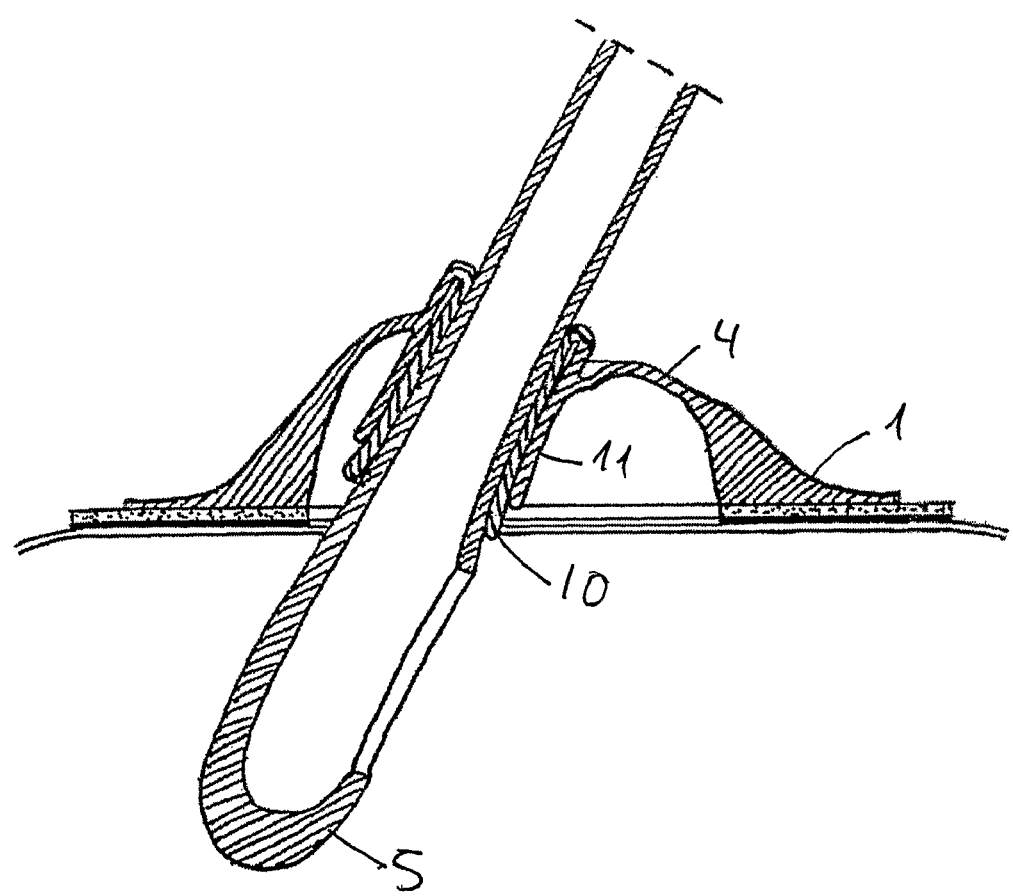
Figure 10B:
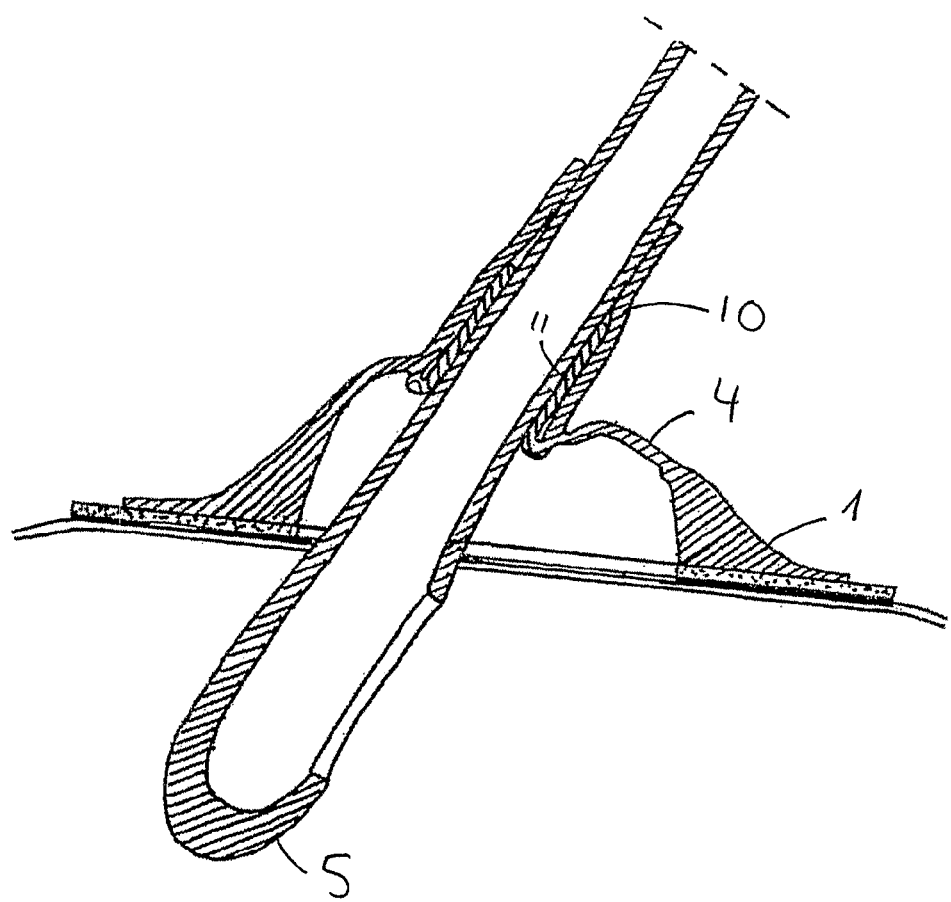
Figure 10C:
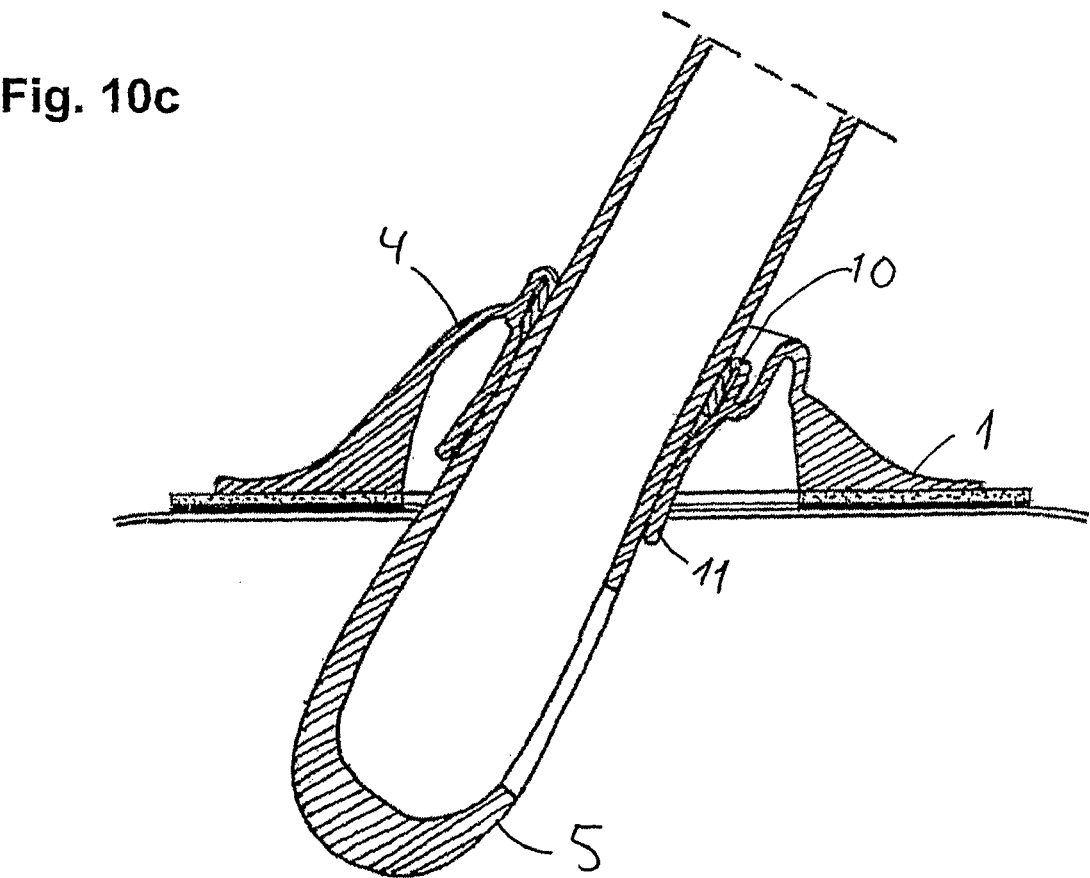
Figure 10D:
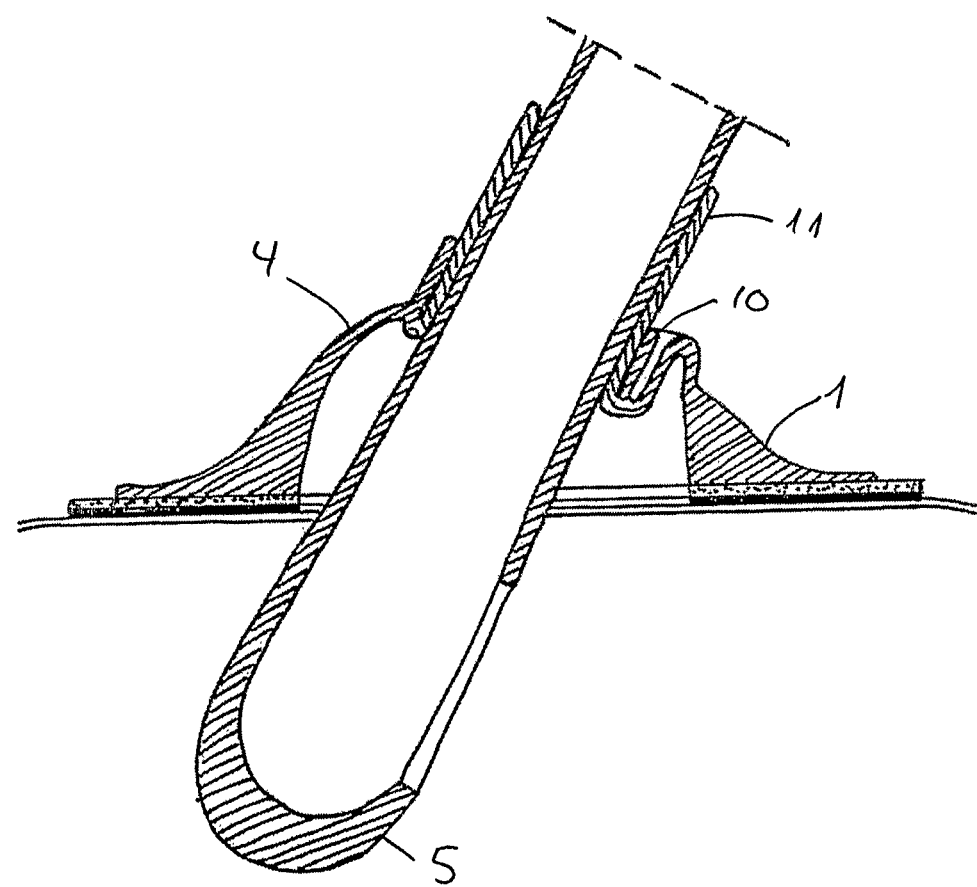

In FIGS. 9a and 9b is disclosed an embodiment of the invention, wherein the access port is provided with an upper sleeve lip (10) and a lower sleeve lip (11), with respect to the point (12) where the membrane connects to the sleeve portion. In the shown embodiment, one of the sleeve lips (10, 11) has a diameter smaller than the other, rendering it possible to adapt the port to different sizes of conduits. When the conduit is inserted through the port, one of the sleeve lips (10, 11) may invert as shown in FIGS. 10a-d. The orientation of the inversion depends on the movements of the conduit. If the conduit (5) is entered into the aperture (3) from the top of the port, the upper lip (10) will be dragged, due to friction, in the direction of the movement of the conduit and be turned inside out and forming a double layer of lips (10, 11). In FIG. 10a the conduit (5) has been inserted in the port, and in FIG. 10b the conduit is pulled slightly backwards, thus inverting the orientation of both lips. The double layer sleeve lips (10, 11) enhance the force by which the sleeve portion affects the conduit and provides a better seal. As can be seen from the Figures, the slightly curved configuration of the membrane portion (4) facilitates excess material of the membrane providing high flexibility, and minimum stress induced in the port. FIGS. 10c and 10d show a preferred embodiment of the invention wherein the upper sleeve lip (10) is shorter than the lower sleeve lip (11). In this embodiment the tightening forces of the of the sleeve portion (2) is enhanced during the inversion of the longest (in this case lower lip) lip supported by the shorter upper lip (10) lying on top and adding even more pressure to the conduit (5). It is preferred that the lip being inverted is longer then the other lip.

In one embodiment of the invention, one of the sleeve lips may be attached to the access port by a weakened line, facilitating that at least a part of the lip may be torn off. In this way the port may be adapted to different sizes of conduits.

Attempt to compensate for the change in material properties—by designing the access port, so that the sleeve lip cannot be pulled back with a reasonable pull in the catheter—resulting in a sleeve positioned upwards is difficult as the friction of the material used for the port is important, a material with a high friction may cause the sleeve lip to invert easily when the conduit is pulled, while a low friction may render it possible to have the sleeve lip stay in place.

The friction of the material may be altered by additives to the composition or to the surface of the access port. The additives may be active so they migrate to the surface of the part or be mixed in the compound and stay dispersed in the material.

EXAMPLES

The position and dimensions of the sleeve portion is important in order to obtain an optimum sealing against a conduit. Different samples have been tested in order to identify the critical properties.

The material for the access port has been stored at 23° C. or 40° C. for 15 month at 100% humidity and tested afterwards up to a pressure on 0.03 bar.

The samples have been tested for providing perfect sealing under conditions similar to use on a fistula/wound collection pouch, for 3 days at 100% humidity at 40° C. It is important to test the samples under such conditions, as these reflect the condition the access port may be used under. Catheters or conduits may stay inserted for days, and a port that may be leakage proof the first day, may be influenced by the temperature, stress and humidity and thus become less leakage proof over time.

The tests showed that most materials would change their properties over time and temperature. An aperture designed for easy access of a specific range of catheters, began to loose its grip over time due to this change of properties, resulting in a decrease in the force [N] transferred from the center sleeve to the conduit making the seal.

To compensate for this change of properties, the sleeve may be positioned downwards to assure optimum sealing at high pressures (0.01 bar or lower—0.15 bar).

Example A

Importance of the Positioning of the Sleeve

Figure 7A:
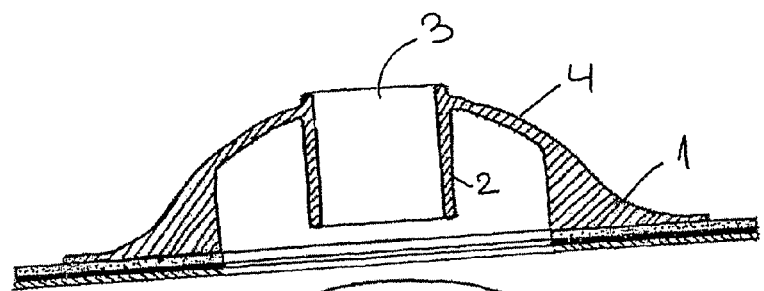
FIGS. 7a and 7b show an embodiment of the invention.
Figure 7B:
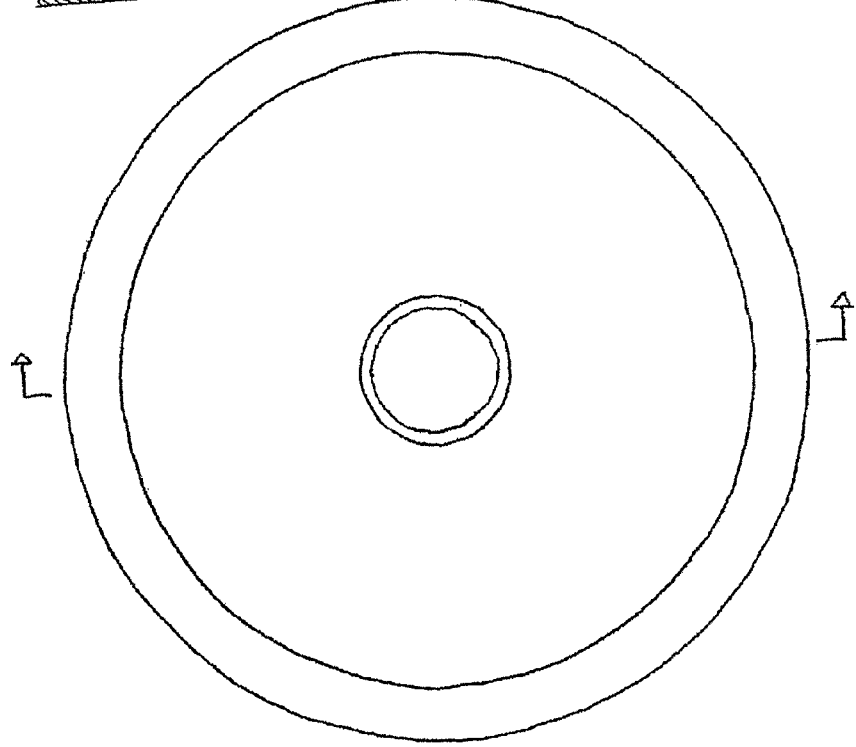

An access port with a simple design as illustrated in FIGS. 7a and 7b was prepared from SEBS. All dependent on the size of the starting aperture in the access port and the size of the inserted catheter the test result may vary slightly. Test has shown that most very flexible materials will show same result even if a much bigger catheter is inserted through same small starting aperture.

In this example the wall thickness of the sleeve is 0.6 mm and the sleeve length is 8 mm and having a starting aperture of 5 mm. Stored for 3 days at 100% humidity at 40° C. with a CH18 (6 mm) catheter inserted in the access port.

TABLE 1

| Sleeve position | Test at 0.05 | Test at 0.15 bar | Test at 0.3 bar |
| --- | --- | --- | --- |
| Upwards | Risk of leakage | Leakage | Leakage |
| Downwards | No leak | No leak | No leakage or minimal risk of leakage |

Results with the sleeve portion positioned downwards—a significant improvement of the sealing, same result can be achieved even when rotating the catheter as long the sleeve is positioned downwards. If the catheter at the same time is fixated to the product during use this reduces the risk of leakage even more making optimum sealing between the catheter and the access port even though the material has altered properties due to the storage conditions.

By having the sleeve positioned upwards the risk of leakage increases when pulling the catheter. This can be compensated in different ways. Optimal sealing can be achieved even with a sleeve positioned upwards. To achieve this the drain port can be fixed by external means such as adhesive strips, string or a clamp.

Example B

Figure 8A:
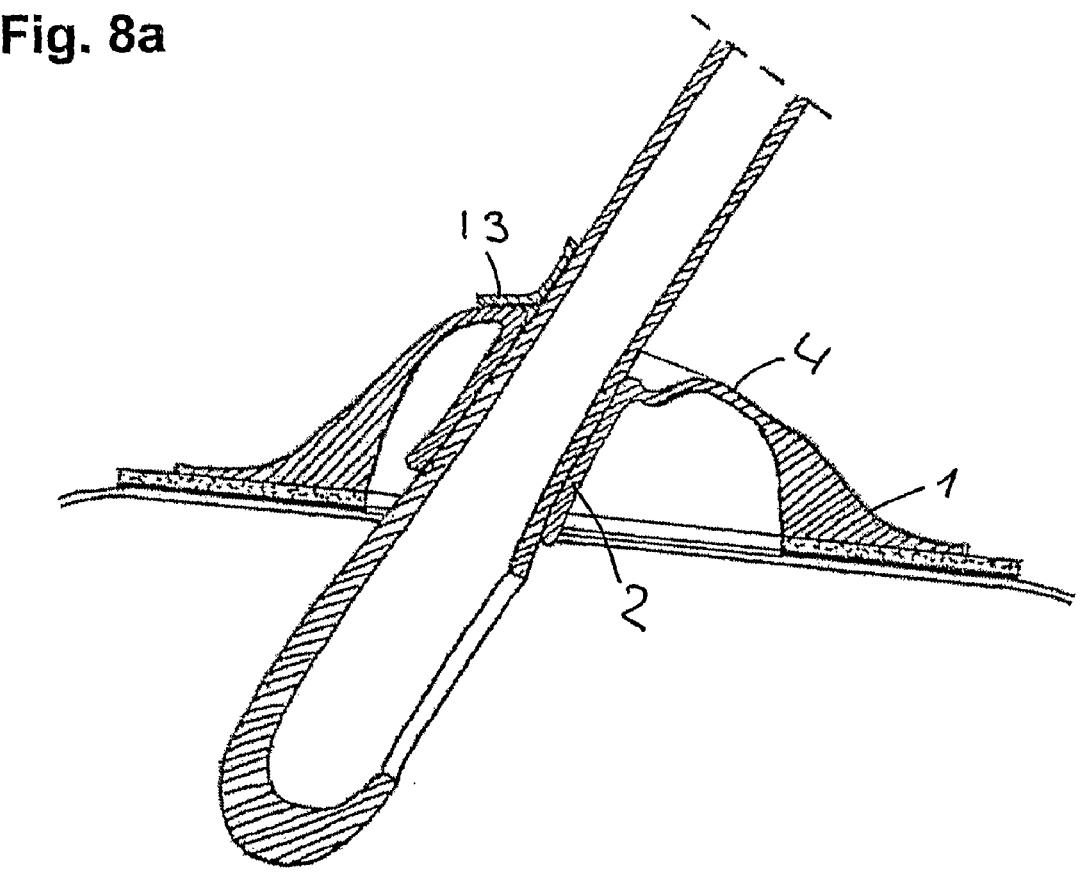
FIGS. 8a and 8b show an embodiment of the invention.
Figure 8B:
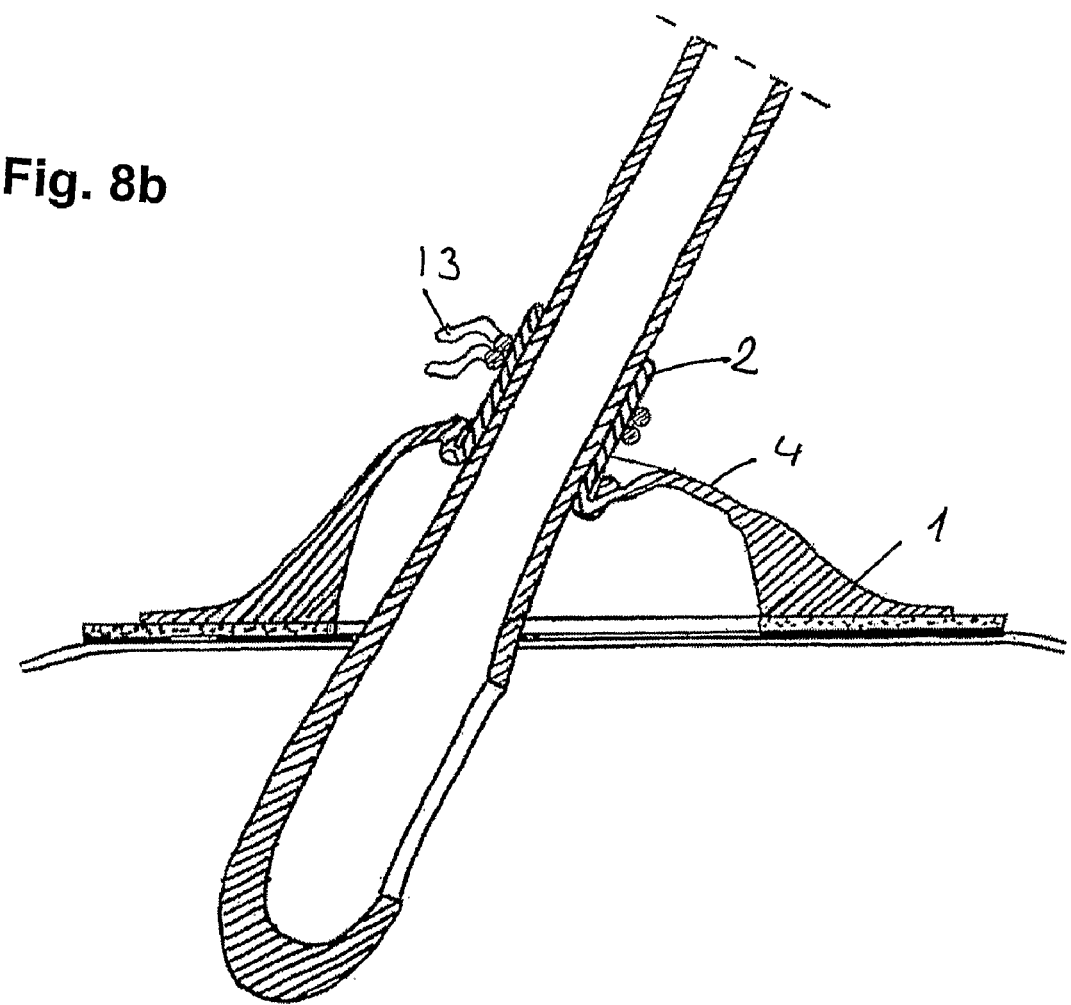

Attempt to Compensate for the Change in Material Properties—with Designs where the Sleeve is Positioned Upwards In FIGS. 8a and 8b is shown solutions based on use of fixation means, which can fixate the access port to the catheter, preventing the catheter in moving upwards and maintaining perfect sealing by obtaining a constant pressure between the catheter walls and the sleeve of the access port.

The solution involves either a repositionable string, cord, clamp, tape or other fixations means (12). It is preferred that the fixation means can be tightened all around the catheter.

Example C

Attempt to Compensate for the Change in Material Properties—by Making the Sleeve Longer, Attempt to Make the Position of the Sleeve Less Important—Towards a More Leak Proof Design The wall thickness of the sleeve is 0.6 mm and the upper sleeve lip length is 1 mm, and the aperture is 5 mm at start. Stored for 3 days at 100% humidity at 40° C. with a CH18 (6 mm) catheter inserted in the access port. Again the same results have been seen with insertion of larger catheters.

TABLE 2

| Lt - Length of bottom sleeve | Test pressure 0.05 bar | Test pressure 0.10 bar | Test pressure 0.15 bar | Test pressure 0.3 bar |
| --- | --- | --- | --- | --- |
| 6 mm | Leakage | Leakage | Leakage | Leakage |
| 8 mm | Risk of Leakage | Leakage | Leakage | Leakage |
| 10 mm | Minimal Risk of leakage | Some of leakage | Risk of leakage | Leakage |
| 12 mm | No leakage | Minimal of leakage | Risk of leakage | Leakage |

The invention claimed is:

1. An access port for enabling passage of a conduit through a partition wall, said port comprising a sleeve portion defining an aperture for receiving the conduit there through, a flange portion for attachment to the partition wall, said flange portion encircles the sleeve portion and has a greater diameter than the sleeve portion, and a membrane portion connecting the flange portion and the sleeve portion, wherein the sleeve portion comprises a cylindrical upper lip having a first diameter and extending upwards and a cylindrical lower lip having a second diameter and extending downwards relative to where the membrane portion connects with the sleeve portion, the first diameter different from the second diameter and the sleeve portion flexible such that at least one of the cylindrical upper lip and the cylindrical lower lip is invertible into the aperture toward an opposite one of the sleeve lips.

2. A port according to claim 1 wherein the lower sleeve lip is longer than the upper sleeve lip.

3. A port according to claim 1 wherein the upper sleeve lip is longer than the lower sleeve lip.

4. A port according to claim 1 wherein at least one of the sleeve lips is configured to turn inside out to a position alongside the opposite one of the sleeve lips.

5. A port according to claim 1 wherein the first diameter of the cylindrical upper lip is smaller than the second diameter of the cylindrical lower lip.

6. A port according to claim 1 wherein at least a part of the upper or lower sleeve lip can be torn off by a weakened line.

7. A port according to claim 1 wherein the length of the sleeve portion is larger than the diameter of the sleeve portion.

8. A port according to claim 1 wherein the membrane portion has a substantially uniform thickness.

9. A port according to claim 1 wherein the sleeve portion has a substantially uniform wall thickness.

10. A port according to claim 1 wherein the height of the port is smaller than the width of the access port.

11. A port according to claim 1 wherein the inner diameter of the flange portion substantially corresponds to the outer diameter of the membrane portion.

12. A port according to claim 1 wherein the sleeve portion is thicker than the membrane portion.

13. A port according to claim 1 wherein the sleeve portion has the form of a cylinder having a wall thickness at least equal to the thickness of the central part of the membrane portion and having a length longer than the same thickness.

14. A port according to claim 1 wherein the port comprises a closing device.

15. A port according to claim 14 wherein the closing device is an adhesive label.

16. A port according to claim 14 wherein the closing device is a plug.

17. A port according to claim 16 wherein the plug is an integrated part of the port.

18. A port according to claim 17 wherein an elongated part of the sleeve portion between the sleeve and the plug comprises a weakened line for breaking.

19. A port according to claim 18 wherein the weakened line is next to plug.

20. A port according to claim 18 wherein the weakened line is at a distance from the plug.

21. A port according to claim 18 wherein the weakened line is in the form of a ridge or groove.

22. A port according to claim 1 wherein the port is prepared from thermoplastic elastomer.

23. A port according to claim 1 wherein the port is prepared from a material chosen from the group of silicones, vulcanized rubber materials or blends/copolymer thereof.

24. A port according to claim 1 wherein the port is prepared from a material comprising SEBS (styrene ethylene butylene styrene block copolymer).

25. A port according to claim 1 wherein the port is prepared from a material chosen from the group of silicone foams, PU-foams and PE-foams.

26. A port according to claim 1 wherein the port is prepared from a material having a hardness of between 30 and 40 Shore A.

27. A port according to claim 1 wherein the port is prepared from a material having a density between 0.8 and 1.2 g/cm$^3$.

28. A port according to claim 1 wherein the port is prepared from a material having an elongation of at least 200%.

29. A port according to claim 1 wherein the port is prepared from a material having an elongation of at least 400%.

30. A port according to claim 1 wherein the port is prepared from a material having an elongation of at least 600%.

31. A port according to claim 1 wherein the flange portion is provided with an adhesive layer.

32. A port according to claim 1 wherein the port is welded to the partition wall.

33. A port according to claim 1 wherein the partition wall is the skin.

34. A port according to claim 1 wherein the partition wall is a medical device.

35. A port according to claim 1 wherein the conduit is a catheter.

36. A port according to claim 1 wherein the conduit is a drain tube.

37. A port according to claim 1 wherein at least one of the upper lip and the lower lip is invertible into the aperture to form a double-thickness sleeve around the conduit.

38. A port according to claim 37 wherein the both the upper lip and the lower lip are movable to form the double-thickness sleeve around the conduit.

* * * * *